(12) United States Patent
Chien (10) Patent No.: US 6,415,671 B1
(45) Date of Patent: Jul. 9, 2002

(54) PNEUMATIC GOLF CLUB TESTING MACHINE

(76) Inventor: Kun-Lin Chien, No. 15, Ln. 462, NanYing Rd., NanTou (TW)

( * ) Notice: Subject to any disclaimer, the term of this patent is extended or adjusted under 35 U.S.C. 154(b) by 0 days.

(21) Appl. No.: 09/779,654

(22) Filed: Feb. 9, 2001

(51) Int. Cl.[7] .............................................. G01N 19/00
(52) U.S. Cl. ..................................... 73/865.9; 73/12.08
(58) Field of Search ............................ 73/11.04, 12.01, 73/12.04, 12.05, 12.09, 865.9, 12.08

(56) References Cited

U.S. PATENT DOCUMENTS

| | | | |
|---|---|---|---|
| 3,855,842 A | * 12/1974 | Imabori et al. | 73/11.01 |
| 4,175,440 A | * 11/1979 | Booth | 73/488 |
| 4,875,293 A | * 10/1989 | Wakefield | 33/508 |
| 5,497,650 A | * 3/1996 | Chien | 73/12.07 |
| 5,696,312 A | * 12/1997 | Lee et al. | 73/12.02 |

* cited by examiner

Primary Examiner—Max Noori
(74) Attorney, Agent, or Firm—Troxell Law Office PLLC (57) ABSTRACT

A golf bombarding testing machine, which is mainly composed of a golf shooting apparatus, a club holding device, a ball-head holding device, a vibration-reducing device, a ball cage and a machine frame. By the club holding device or the ball-head holding device to fix the club or the ball-head, and by the application of the golf shooting apparatus to shoot out a golf which then hits the ball-head of the said club will reach the double functions of quick test for the ball-head or the connection strength between the club and the ball-head. Furthermore, by the installation of the vibration-reducing device, may greatly reduce the club's vibration caused by the hit on the ball-head and conduct the next test of hitting as soon as possible to increase the number of test in an unit time period.

5 Claims, 8 Drawing Sheets

PNEUMATIC GOLF CLUB TESTING MACHINE

BACKGROUND OF THE INVENTION

1. Field of the Invention

The present invention relates to a golf bombarding testing machine, especially for a golf bombarding testing machine, which can quickly test a ball-head and the strength of a club.

2. Description of the Prior Art

Figure 1:
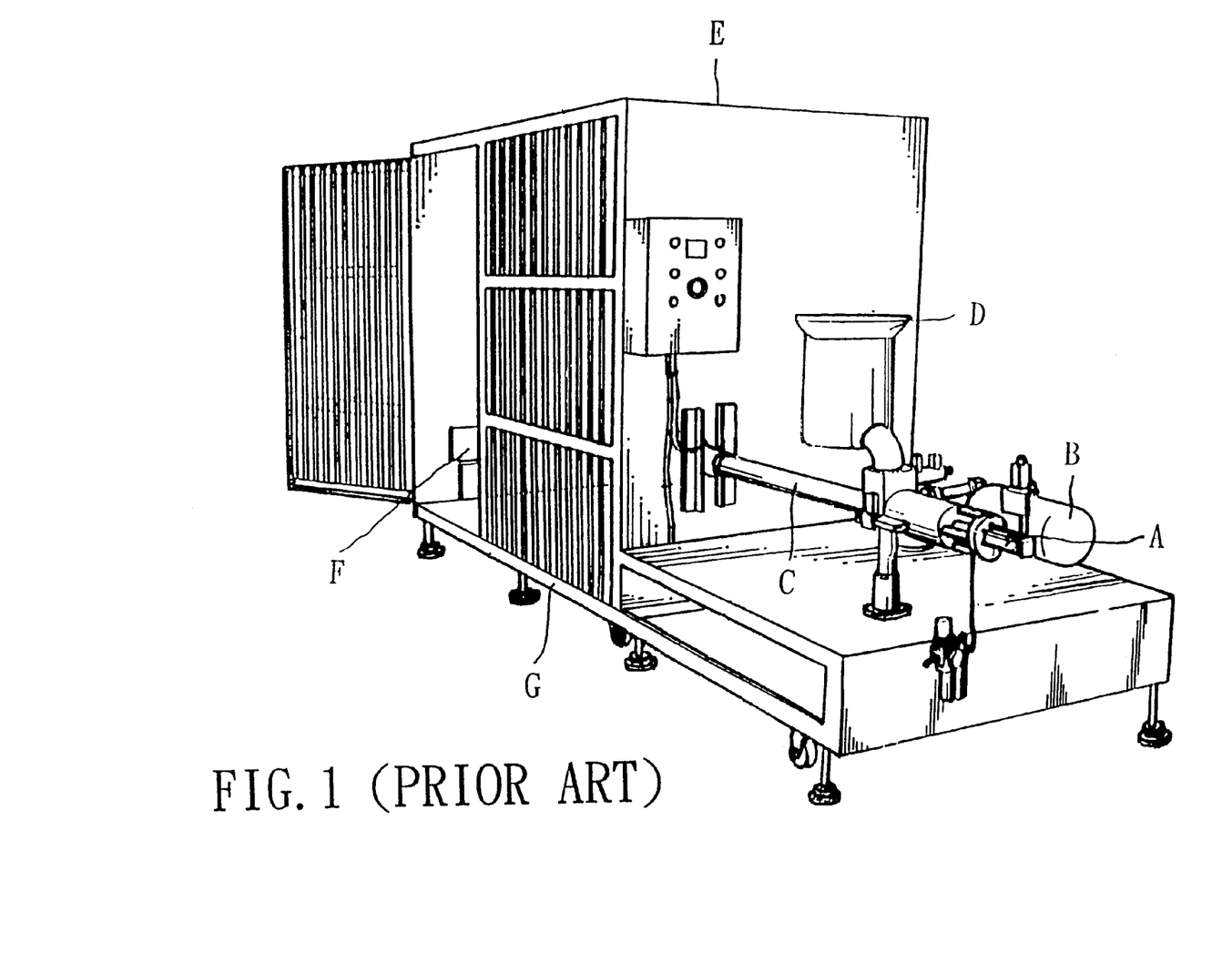
FIG. 1 is a three-dimension illustration for the prior structure.
Figure 2:
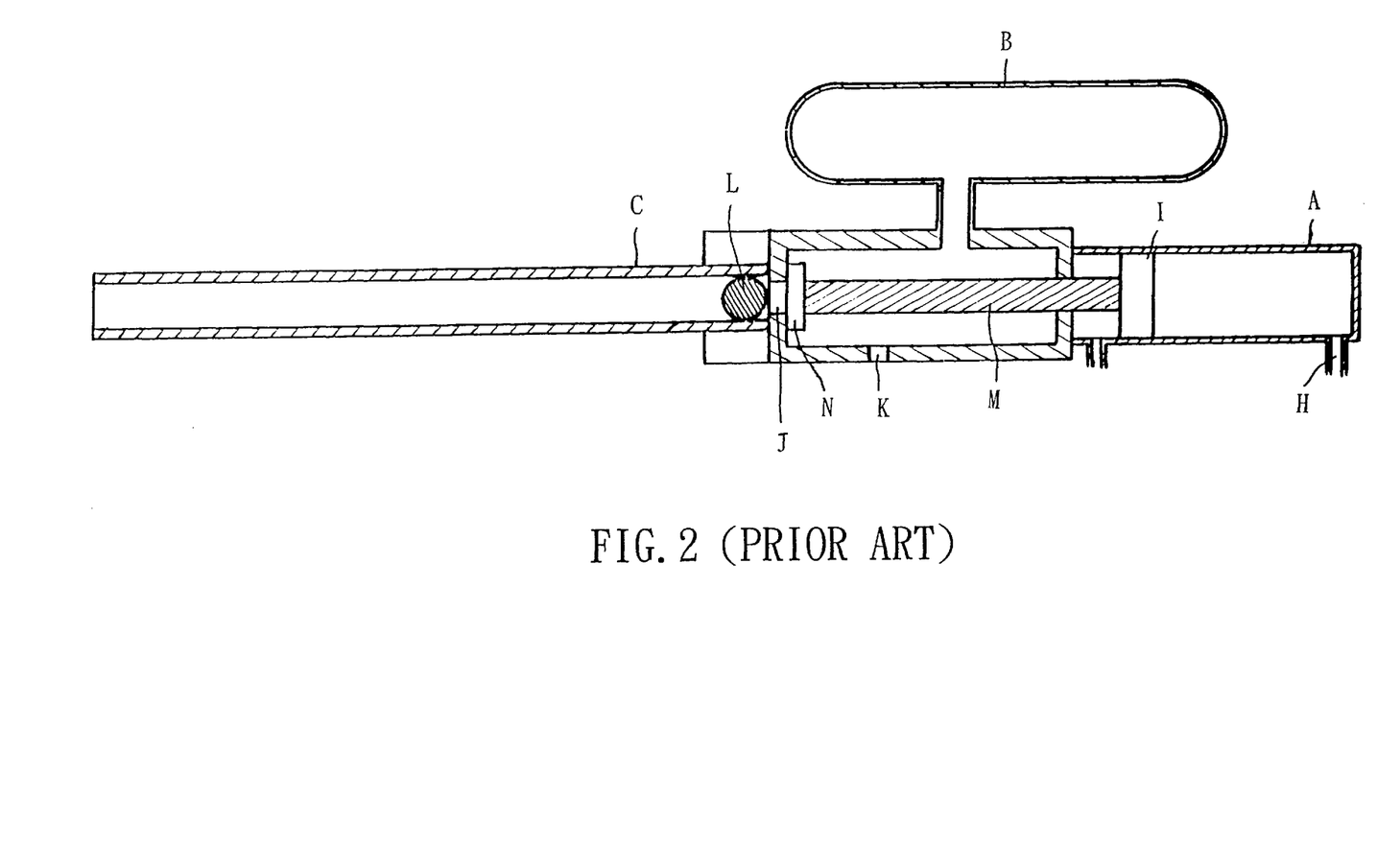
FIG. 2 is a section-view illustration for the prior structure.

Accordingly, due to the narrow land and the crowded population of our country and the difficulty to get domestic land, additionally, the specially interactive relationship between the politician and the businessman in Taiwan, the golf sport is hitherto regarded as a noble sport in this country. The prices of the relative articles for golf are always correspondingly higher than those of other kinds of balls, and the relative articles for golf may maintain a fixed high profit. In like manner, the requirement of the golf players for the quality of ball appliance is correspondingly severe. Therefore, the manufacturers of relative products of these kinds also establish a product testing flow path of extremely severe quality-control for the produce produced by themselves. Wherein, the quality of the superiority and inferiority of the club relative directly to the record of club-swing is further not in least ignored. Therefore, many manufacturers of the club all install a machine for the quality test aiming the club and the ball-head. Applying the machine makes repetitious hits to examine and test the strength of the ball-head and the club. And, the prior testing device is a kind of robotic arm aiming the strength of a club. Mainly in the prior art, by a machine capable of holding and fixing a club simulates a motion of hitting ball of swing club. By a continuous conduct of motion of hitting ball of swing club tests the degree of endurance of usage of a club. However, the above-said structure still has many shortcomings in practical operation, for example: the robotic arm can only test for a single direction and because the club will happen vibration by itself during hitting ball of swing club, it is possible to execute the next motion of swing club only after the disappearance of the vibration. According to the currently real operation test, the testing speed of the fore-said robotic arm is about five times per minute (the time interval for each ball hitting is about twelve seconds). And, the testing procedure of the current general manufacturers adopts one thousand times of test on the front, middle, and rear parts of the ball-head. Follow this by analogy, it can reason that it takes about ten hours for a test of a club to determine whether it is passed or not. Not only it consumes a lot of time, but there is no any recovery apparatus may aim the motion of the automatic recovery of the hit golf ball during test period, and it must be executed by human labor to do the work of recovery. This is the reason why this inventor had submitted a patent application of invention entitled "PNEUMATIC GOLF CLUB TESTING APPARATUS" to your esteemed bureau on Apr. 19, 1995. And, the patent, been authorized by your esteemed bureau (the U.S. Pat. No. 5,497,650), which comprises: a pneumatic cylinder A, an accumulator B, a cannon pipe C, a ball collecting barrel D, a ball cage E, a ball-head fixer F and a machine frame G. The major operation procedures are: fixing the test-intended ball-head on the ball-head fixer F; by a compressed air entering from the second air intake port H of the pneumatic cylinder A into the cylinder A to push the piston I to move forward; and, by a valve of the front end of the piston rod to close the exhaust hole J which is a connection between the front end of the accumulator B and the cannon pipe C; as the shooting starts, then the compressed air is delivered into the first air intake port K of the front end of the pneumatic cylinder A to make the piston I move quickly backward and open the valve N of the front end of the piston road M; in this time, then the compressed air of the accumulator B can instantly release an energy to shoot out the golf L from the cannon pipe C to hit directly on the golf ball-head held inside the ball-head fixer F to reach the object of a quick test. However, the fore-said structure can test only a ball-head and that is a little insufficiency in the function and in the range of the test. On the other hand, the shot golf will fall into the ball cage and it must depend on an operation personnel to pick up the golf L from the ball cage E and from beginning discharge it into the ball collecting barrel D. In application, there is still room for study and improvement to further suit the function of practical application.

Therefore, there are defects for the test device of the golf club of the prior robotic arm for the application of the practical operation, for example: capability of test only in single direction, the test time being too long and incapability of automatic recovery of the golf, etc., which are needed to be studied and improved eagerly by ourselves.

According to all the items of the shortcomings of the fore-said prior testing device for a golf club, and by the experience of this inventor of the engagement of several years in study, production and sales for this kind relative products, and a thorough scrutiny with a quiet concentrated mind, and an match with an application of academic theory, and through continuous study with effort, testing and improvement, finally address the present invention of a kind of reasonable design and capable of effective improvement for the above-said defects.

SUMMARY OF THE INVENTION

The major object of the present invention is to provide a golf is bombarding testing machine, which is mainly composed of a golf shooting apparatus, a club holding device, a ball-head holding device, a vibration-reducing device, a ball cage and a machine frame. By the club holding device or the ball-head holding device to fix the club or the ball-head, and by the application of the golf shooting apparatus to shoot out a golf which then hits the ball-head of the said club will reach the double functions of quick test for the ball-head or the connection strength between the club and the ball-head.

The secondary object of the present invention is to provide a golf bombarding testing machine, wherein, by the installation of the vibration-reducing device, may greatly reduce the club's vibration caused by the hit on the ball-head and conduct the next test of hitting as soon as possible to increase the number of test in an unit time period.

The another object of the present invention is to provide a golf bombarding testing machine, wherein, a golf shooting apparatus is composed of a pneumatic cylinder, an accumulator, a cannon pipe, a ball collecting barrel and a conveyer. By the installation of the fore-said conveyer may collect all the shot golfs, then applying the conveyer to transport the golfs to the ball collecting barrel and to the cannon pipe in sequence, and by the pneumatic cylinder and the accumulator shoot out the golf through the cannon pipe and reach a preferably automatic function.

Furthermore, the another object of the present invention is to provide a golf bombarding testing machine, wherein, the invention has a control box which is simultaneously matched with induction machine and counter, which are arranged in each one of the different devices, and by which receive signal and control timing of the motion of each device, and automatically shut down the unnecessary power (e.g. conveyer) after the completion of the test to obtain the most effective testing function.

BRIEF DESCRIPTION OF THE DRAWINGS

For your esteemed review committee to further understand and recognize the object, the characteristic and the function of the present invention, a detailed description matching with several figures are as as following.

DETAILED DESCRIPTION OF THE PREFERRED EMBODIMENT

Figure 3:
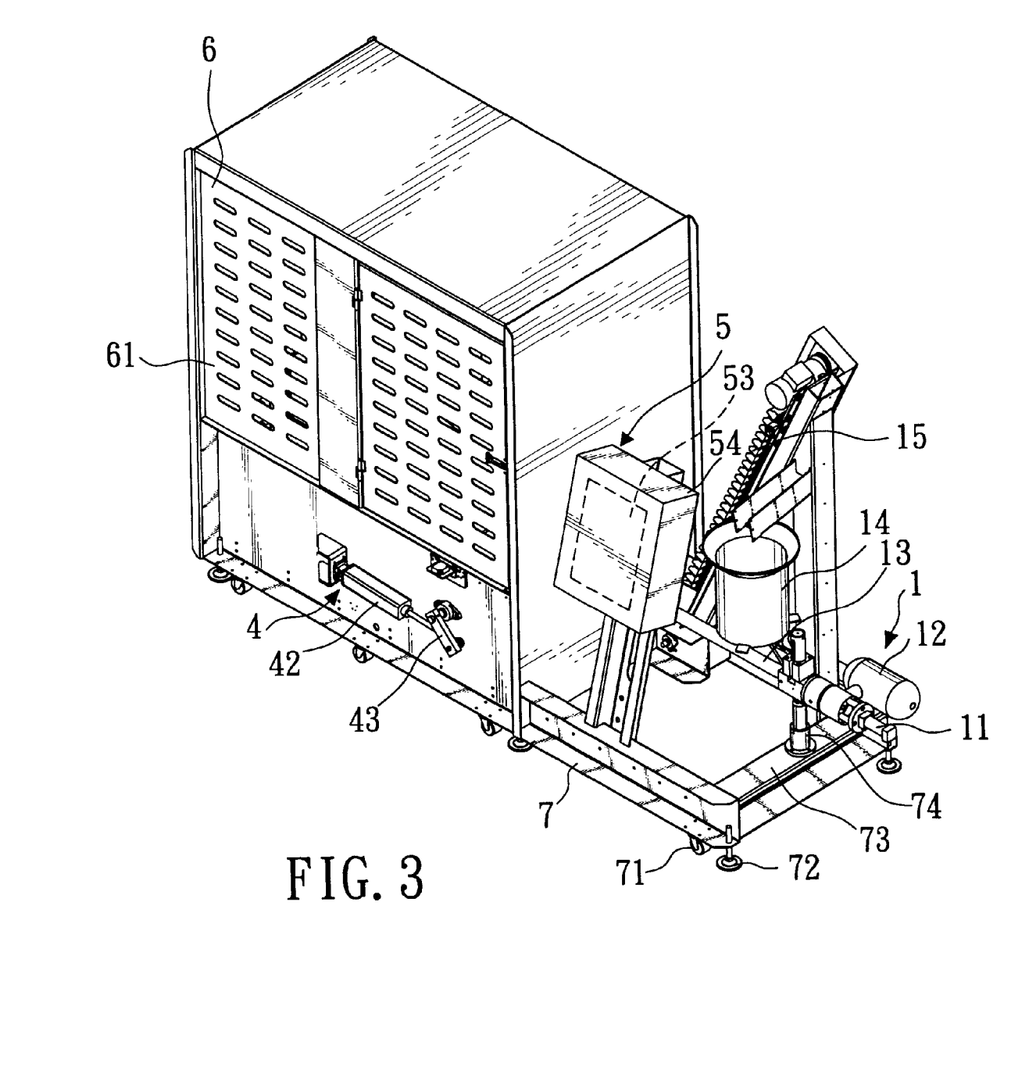
FIG. 3 is an outer-view three-dimension illustration for the present invention.
Figure 4:
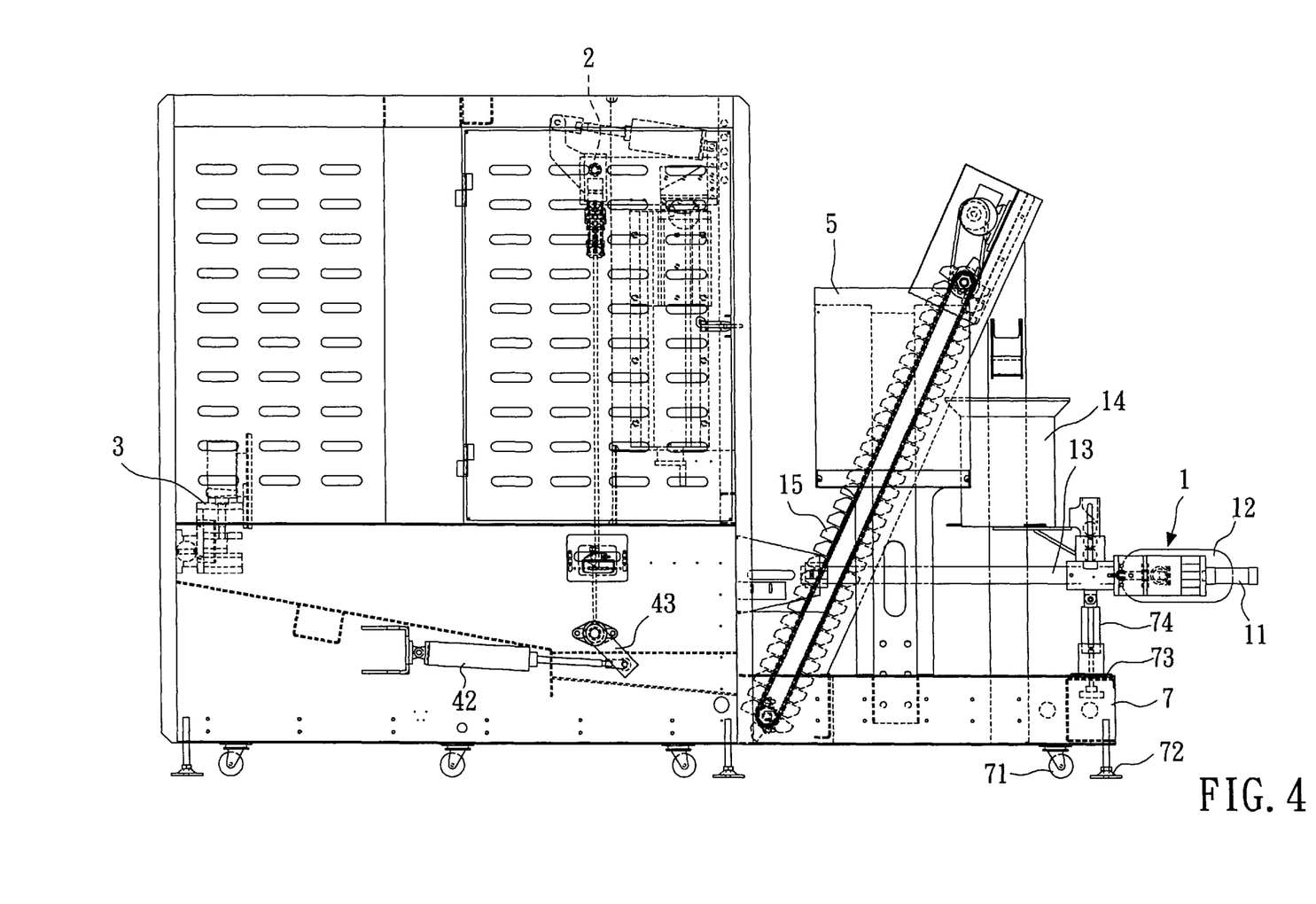
FIG. 4 is a plane illustration for the present invention.

Please refer to FIG. 3 and FIG. 4, which are three-dimension decomposing illustration and three-dimension composing illustration of the present invention. The present invention mainly is composed of a golf ball shooting apparatus 1, a club holding device 2, a ball-head holding device 3, a vibration-reducing device 4, a sense control unit 5, a ball cage 6 and a machine frame 7. Wherein, a control box is fixed on the rear side-wall of the ball cage 6. And, the golf shooting apparatus 1 is composed of a pneumatic cylinder 11, an accumulator 12, a cannon pipe 13, a ball collection barrel 14 and a conveyor 15. Plural rollers 71 for facilitating to move and dish bases 72 for support are installed under the machine frame 7. Above one side of the machine frame 7, there is a platform face 73 in plate-shape. Above the platform face 73, there are elements of the horizontally installed pneumatic cylinder 11, the accumulator 12 and the cannon pipe 13 etc., which are supported by one support rod 74. Wherein, the accumulator 12 is installed in the rear of the cannon pipe 13. By the control of the pneumatic cylinder 11 compresses the air and stores it, afterwards, at the twinkle of an eye, discharges the stored, compressed air and conducts the air into the cannon pipe 13. And, the ball collection barrel 14 is installed above the rear of the cannon pipe 13. A conduction pipe conducts the golf ball which is stored inside the interior of the ball collection barrel into an automatic golf feeding port which is located between the accumulator 12 and the cannon pipe 13. When the golf ball falls into the feeding port, it may automatically activate a sensing apparatus to start to make the compressed air of the accumulator 12 be conducted into the cannon pipe 13 and shoot out the golf ball. The shot out golf ball hits upon the ball-head 9 held by the ball-head holding device 3 inside the ball cage 6 or the club held inside the club holding device 2 to accomplish the dual functions of the quick test on the ball-head or the connection strength between the club and the ball-head. Furthermore, by the installation of the fore-said conveyer 15 may make the shoot-out golf ball automatically roll to the front of conveyer 15, and by which transports the golf ball to the ball collecting barrel 14 and in sequence to the cannon pipe 13, and by the pneumatic cylinder 11 and accumulator 12 shoots out the golf ball form the cannon pipe 13 to accomplish the more preferably automatic function.

Of the present invention, the sense control unit 5, installed inside the control box 54, is mainly composed of at least one induction element, a counter and the IC board 53. The sense control unit 5 matches with the induction element and the counter which are installed on each different device, and by the received signals automatically controls the timing of the motion of each device, and automatically shuts down the unnecessary power (e.g. the conveyer 15) to acquire the optimal function of power saving and testing.

Figure 5:
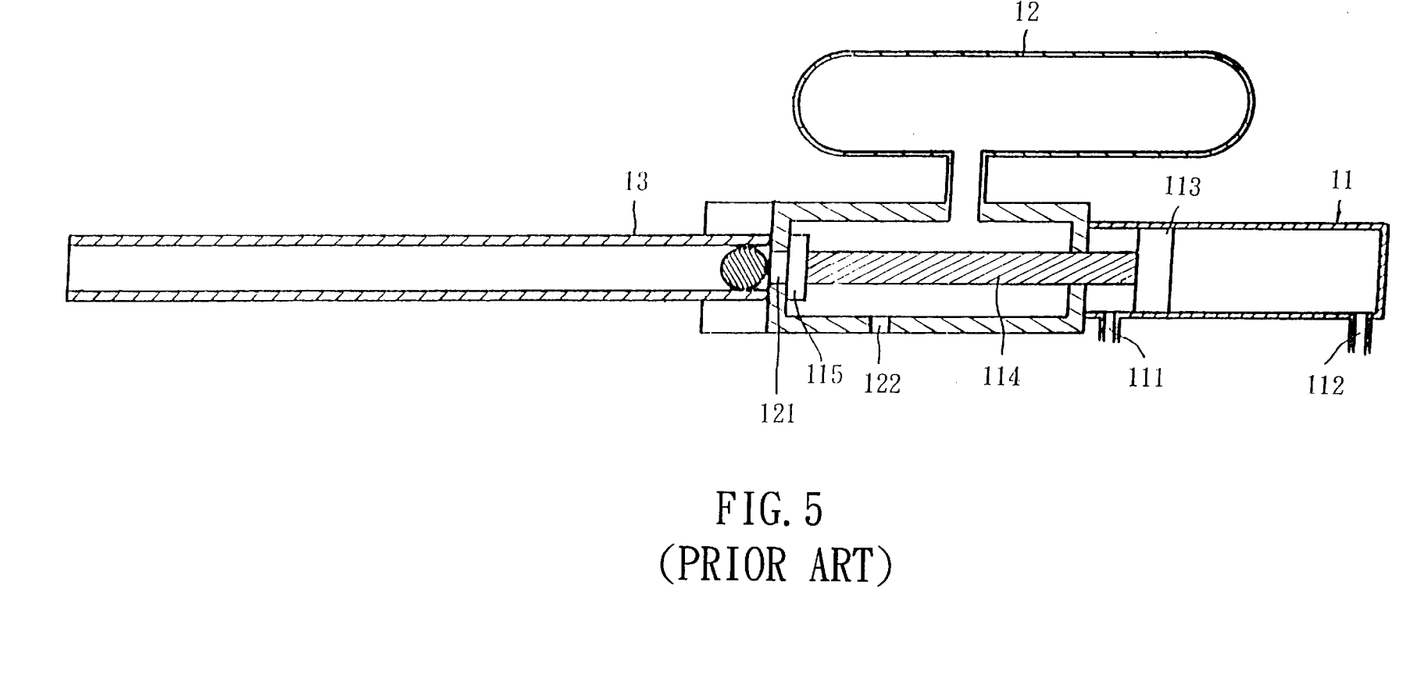
FIG. 5 is the section-view illustration for the golf shooting apparatus of the present invention.

The above-said golf shooting apparatus 1, in which the compressed air enters the pneumatic cylinder 11 from the second air-intake port 112 of the rear end of the pneumatic cylinder 11 (as shown in FIG. 5). The pressure acts on the piston 113 to make it move forward, and through a valve on the front of the piston closes down the exhaust hole 121 which is a connection between the front end of the accumulator 12 and the cannon pipe 13. The compressed air, of which pressure has been adjusted, from an air intake port 122, is supplied into the accumulator 12 for pressure-storage, and after the completion of above procedure, the air intake port 122 will be closed down to prevent pressure losing. Hereon, a compressed air is supplied into the first air intake port 111 located at the front end of the pneumatic cylinder 11. In the mean time, the pressure, which entered into the pneumatic cylinder 11 and acts on the piston 113, is discharged out through the second air intake port 112. Then, the piston 113 moves backward quickly, in the mean time, the valve is opened up by the piston rod, and the compressed air inside the accumulator 12 releases out energy instantaneously, and which shoots out the golf from the cannon pipe 13, and the flying golf hits the striking face of the ball-head.

Figure 6:
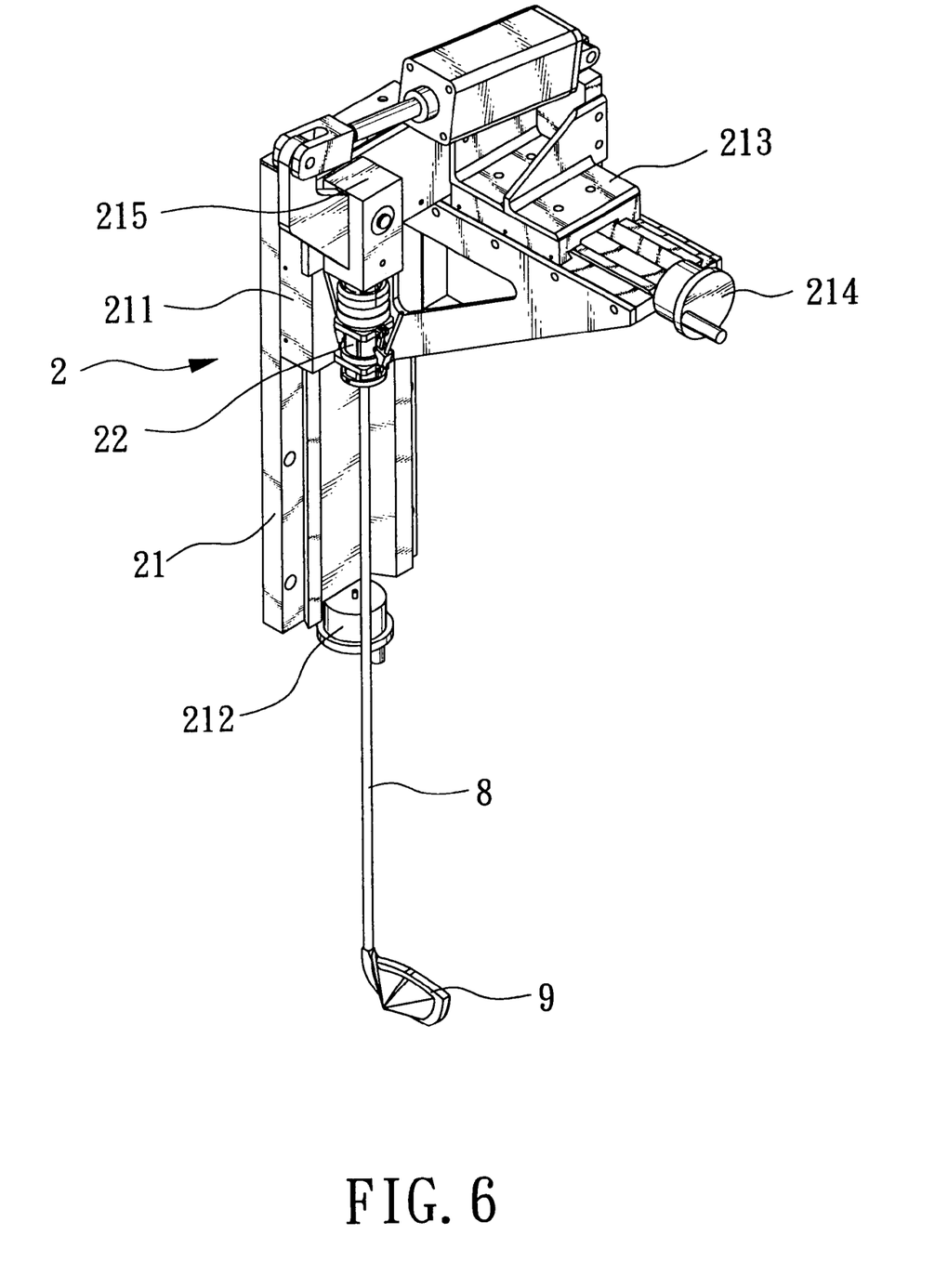
FIG. 6 is the outer-view three-dimension illustration for the club holding device of the present invention.

The club holding device 2 of the present invention is composed of a base seat 21 and a quick clamp-head 22 (as shown in FIG. 6), wherein the base seat 21 may be fixed on the ball cage 6. There is a first sliding seat 211 installed on the base seat 21. The position of the first sliding seat 211 may be adjusted by the application of a first knob 212. There is a second sliding seat 213 installed on the first sliding seat 211. The position of the second sliding seat 213 may be controlled and adjusted by the second knob 214. Furthermore, installed on the second sliding seat 21, a fixed seat 215, on which the quick clamp-head 22 is pivotally installed and may rotate freely. By the application of the fore-said structure of the present invention, it may quickly fix a club in the clamp-head 22 and appropriately adjust its right, left, upper and lower—four positions by rotating the first knob 212 and the second knob 214, and make the golf which is shot out from the golf shooting apparatus 1 may smoothly hit the ball-head of the club.

Further, the ball cage 6 of the present invention is installed on another side of the machine frame 7. The shape of the ball cage 6 can be appropriately varied, but its fundamental function is same. With the cannon pipe 13, the ball cage is connected with the pneumatic cylinder 11, the accumulator 12 etc. The ball cage 6 is substantially a rectangular cage body, in which at least one side is composed of the bars 61 of which interval is less than the diameter of the golf, and in which an openable door is installed, and in which a base plate is in a slanted configuration which can automatically roll the golf inside the ball cage 6 toward the conveyer 15, and the golfs are automatically collected and readily for being applied by the golf shooting apparatus 1. Corresponding to cannon pipe, the farther side of the ball cage, i.e. in a position opposing to the pipe opening of the cannon pipe, a ball-head holding device 3, which is under covered with a prototype-plastic-die-glue, can be applied to hold a golf ball-head.

Figure 7:
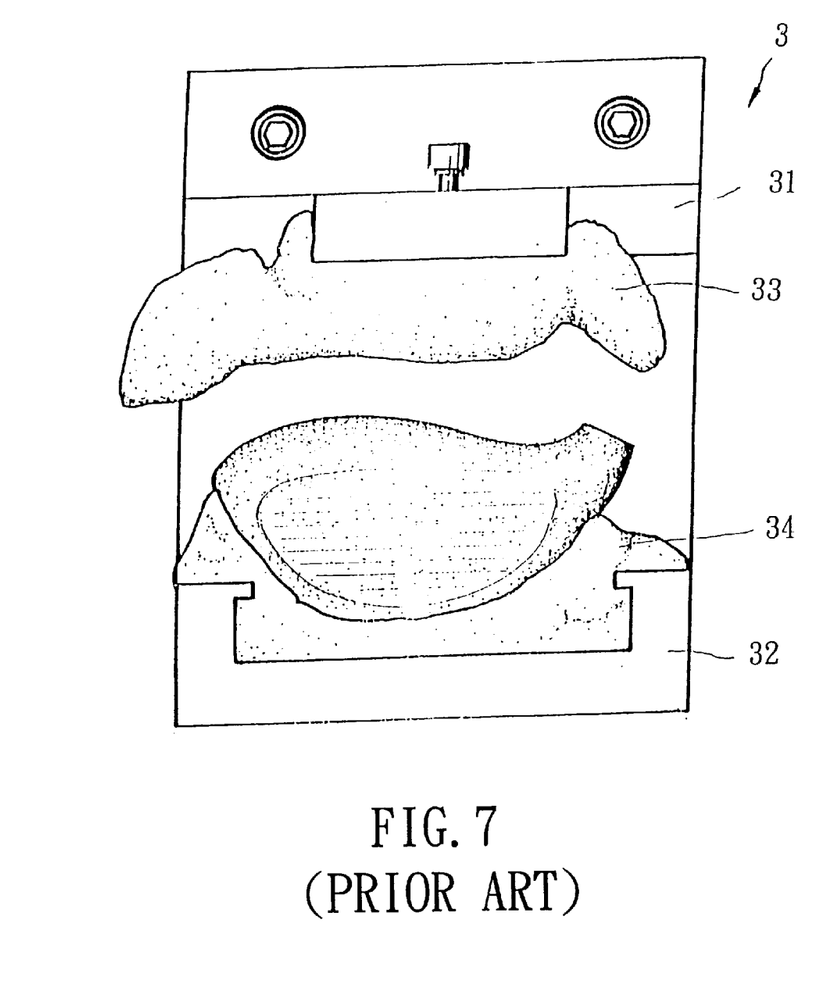
FIG. 7 is the plane illustration for the ball-head holding device of the present invention.

Please refer to FIG. 7, which is a plane illustration of the ball-head holding device of the present invention. The ball-head holding device 3 comprises of an upper-die-seat 31, a lower-die-seat 32, a upper-die 33 and a lower-die 34, wherein the upper-die-seat 31 and the lower-die-seat 32 are made of metallic materials, and the upper-die 33 and the lower-die 34 are made of the prototype-plastic-die-glue. The upper-die 33 and the lower-die 34 are fixed on the upper-die-seat 31 and the lower-die-seat 32 respectively. The method of manufacturing the upper-die 33 and the lower-die 34 by the application a prototype-plastic-die-glue is only: putting the prototype-plastic-die-glue under a hot water of 100° C. temperature to become a state of fluid; pouring the glue to become the shapes of the upper-die 33 and the lower-die 34; letting the dies cool down to room temperature and ready for use. As the ball-head being hold, depending on the conditions of test, the ball-head could be hold completely tight, or increases a bigger gap for the caves of the upper-die and the lower-die, to allow a little room for activity. The method of holding tight is: by the top end of a pneumatic cylinder pushes the lower-die-seat (or the upper-die-seat) to move the lower-die (or the upper-die) upward and enclose the whole ball-head with the upper-die 33 and the lower-die 34. In the traditional method, the striking face of a ball-head must be dissected before it is fixed. However, the fixer of the ball-head of the present invention can hold an entire, undamaged ball-head for testing.

The golf bombarding testing machine of the present invention, by the accumulator 12 compresses the air and stores it, then from the cannon pipe 13 shoots out the golf ball to hit the ball-head held in the ball-head holding device 3 or the striking face of the ball-head 9 inside the club holding device 2. These motions are different from the swing-club motion and may do the destructive test for ball-head 9 without setting up the club. These repetitious operations will test the structure strength of the club-head 9, the connectivity of the base dish and the density of the lacquer. And, since the ball-head holding device 3 is under covered with prototype-plastic-die-glue, so it won't hurt the tested ball-head and can make the test be completed in a most short time and can pick up the sample from the production line anytime and put it to test without waiting until the completion of the set-up and facilitate to proceed the testing operation. Furthermore, not only the present invention may test the ball-head 9, but also may test fixing strength between the club 8 and the ball-head 9. Not only is it unnecessary for manufacturer to pursue additional test machine for testing the connection strength between the club 8 and the ball-head 9, but also the test time of the present invention is shorter than that of the prior product, and it further has more function for practical application.

Figure 8A:
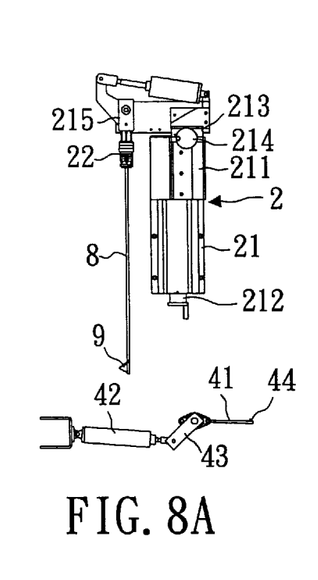
FIGS. 8(A)–8(E) are the motion illustrations for the club holding device and the vibration-reducing device of the present invention.
Figure 8B:
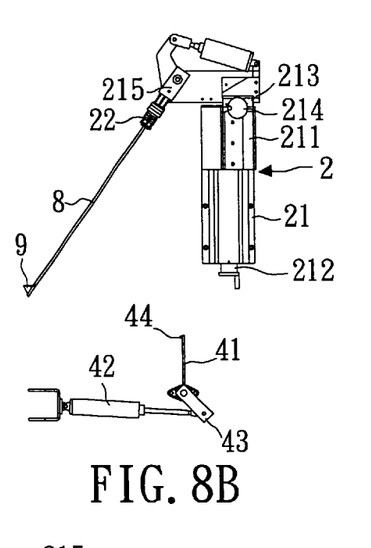
Figure 8C:
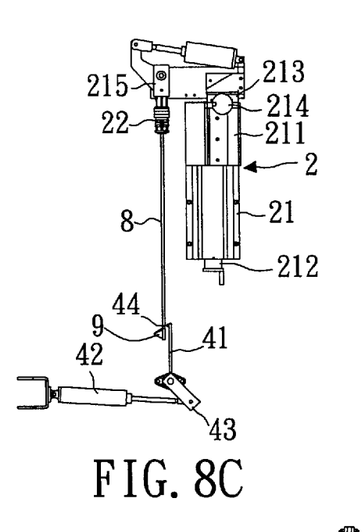
Figure 8D:
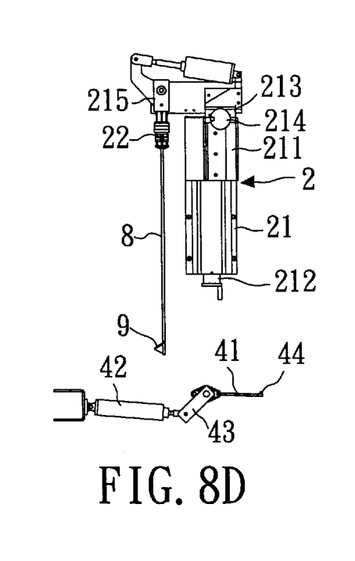
Figure 8E:
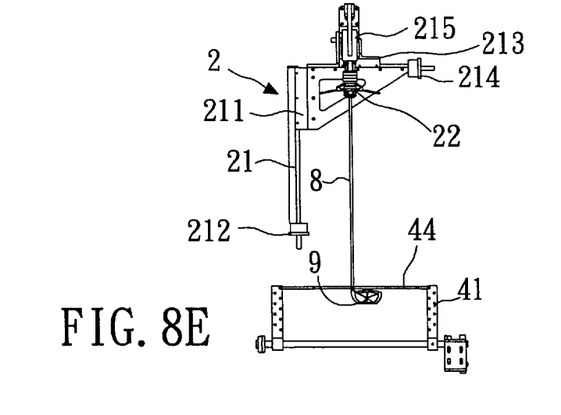

The vibration-reducing device 4 of the present invention is composed of a major body 41, a driving element 42, a connection rod 43 and a vibration-reducing element 44 (as shown from FIG. 8(A) to FIG. 8(E)), wherein the vibration-reducing element 44 is fixed on the major body 41 which is pivotally installed on the machine frame 7 and through the connection rod 43 connects the driving element 42. The driving element 42 may drive the major body 41 to rotate an appropriate angle. As shown in the embodiment of the present invention, applying the pneumatic cylinder drives the major body 41, and applying the vibration-reducing element 44 which is made of a rubber materials. As before the golf ball is shot, the pneumatic cylinder 42 is in a state of contraction and the major body 41 of the reducing device 4 is in a state of almost horizontal (as shown in FIG. 8(A)). When a shot golf ball hits the ball-head 9 fixed on the club holding device 2 and the club 8 will rotate along the direction of the moving golf ball, by the detection of the sense control unit 5 makes the cylinder 42 move forward to make the major body 41 of the vibration-reducing device rotate to a vertical direction (as shown in FIG. 8(B)). When the club 8 swings back, the front end of the club 8 will hit the vibration-reducing element 44 fixed upon the major body 41 (as shown in FIG. 8(C)). Through the vibration-reducing element 44 reaches a purpose of energy absorption to make the club quickly recover and be in a state of waiting for the next hitting test. At this moment, the front end will retreat and make the major body 41 rotate to a horizontal direction (as shown in FIG. 8(D)).

Summarizing above-description, the present invention has the characteristics of the dual functions, which are the direct testing for the club body and ball-head of a golf club. And, through the vibration-reducing device may effectively shorten the time interval between the tests to greatly increase the testing times during unit time and promote the efficiency of its testing. On the other hand, matching with the installation of the conveyer and sensing element make the present invention to reach the function of the totally automatic testing.

What is claimed is:

1. A pneumatic golf testing machine comprising:
   a) a machine frame;
   b) a ball cage mounted on the machine frame and having a base plate slanted toward a first side;
   c) a pneumatic golf ball shooting device mounted on the frame and including a pneumatic accumulator communicating with a cannon pipe and a pneumatically actuated valve controlling communication between the accumulator and the cannon pipe whereby, when a golf ball is present in the cannon pipe and the valve is opened, the golf ball is shot into the ball cage;
   d) a ball collection barrel in communication with the cannon pipe such that golf balls in the ball collection barrel are supplied to the cannon pipe;
   e) a conveyor mounted on the frame and having a first portion positioned so as to receive golf balls from the slanted base plate of the ball cage and a second portion positioned so as to deliver golf balls to the ball collection barrel;
   f) a ball-head holding device mounted inside the ball cage and located such that a ball-head held in the ball-head holding device will be struck by a golf ball shot from the cannon pipe;
   g) a golf club holding device mounted inside the ball cage and including a quick clamp head configured to receive therein a grip portion of a golf club, an adjustment mechanism for adjusting a position of the clamp head such that a ball-head of a golf club held by the clamp head is located so as to be struck by a golf ball shot from the cannon pipe; and,
   h) a vibration-reducing device including a movable vibration-reducing element movable between a first position wherein the vibration-reducing element is out of a path of travel of the golf club held in the clamp head, and a second position in which the vibration-reducing element is in the path of travel of the golf club held in the clamp head.

2. The pneumatic golf testing machine of claim 1 wherein the golf club holding device further comprises:
   a) a base seat;
   b) a first sliding seat slidably mounted on the base seat, the quick clamp head mounted on the first sliding seat; and,
   c) a second sliding seat slidably mounted on the first sliding seat.

3. The pneumatic golf testing machine of claim 1 wherein the vibration-reducing device further comprises a driving element connected to the vibration-reducing element by a connection rod.

4. The pneumatic golf testing machine of claim 3 wherein the driving element comprises a pneumatic cylinder.

5. The pneumatic golf testing machine of claim 3 wherein the vibration-reducing element is made of rubber.

* * * * *